United States Patent [19]

Van Saarloos

[11] Patent Number: 6,056,741
[45] Date of Patent: May 2, 2000

[54] DUAL BEAM LASER ABLATION

[75] Inventor: Paul Phillip Van Saarloos, Innaloo, Australia

[73] Assignee: Lions Eye Institute, Nedlands, Australia

[21] Appl. No.: 08/894,755

[22] PCT Filed: Mar. 1, 1996

[86] PCT No.: PCT/AU96/00108

§ 371 Date: Oct. 21, 1997

§ 102(e) Date: Oct. 21, 1997

[87] PCT Pub. No.: WO96/27335

PCT Pub. Date: Sep. 12, 1996

[30] Foreign Application Priority Data

Mar. 3, 1995 [AU] Australia .................................. PN1534

[51] Int. Cl.⁷ ..................................................... A61B 17/36
[52] U.S. Cl. ........................ 606/5; 606/4; 606/3; 606/10
[58] Field of Search .................................. 606/7, 10, 11, 606/12, 15, 16, 17, 2, 3; 607/88, 89, 94

[56] References Cited

U.S. PATENT DOCUMENTS

| | | | |
|---|---|---|---|
| 4,791,927 | 12/1988 | Menger | 606/10 |
| 5,180,378 | 1/1993 | Kung et al. | 606/2 |
| 5,304,167 | 4/1994 | Freiberg | 606/3 |
| 5,312,396 | 5/1994 | Feld et al. | 606/11 |
| 5,480,396 | 1/1996 | Simon et al. | 606/4 |
| 5,520,679 | 5/1996 | Lin | 606/4 |
| 5,634,922 | 6/1997 | Hirano et al. | 606/10 |

FOREIGN PATENT DOCUMENTS

| | | |
|---|---|---|
| 0 365 754 A1 | 5/1990 | European Pat. Off. . |
| 2 598 608 | 11/1987 | France . |
| 40 04 736 A1 | 8/1991 | Germany . |
| 40 26 240 A1 | 2/1992 | Germany . |
| 42 35 841 A1 | 4/1994 | Germany . |
| WO 93/21843 | 11/1993 | WIPO . |

*Primary Examiner*—Linda C. M. Dvorak
*Assistant Examiner*—Sonya Harris-Ogugua
*Attorney, Agent, or Firm*—Woodcock Washburn Kurtz Mackiewicz & Norris LLP

[57] ABSTRACT

A method for laser ablation of a tissue including directing at least one first pulsed laser beam of ultraviolet light and at least one second pulsed laser beam of infrared light to an area on the tissue to thereby ablate said tissue. The ultraviolet light has a wavelength of between 180 to 225 nm while the infrared light has a wavelength of between 1.4 to 11.0 $\mu$m, and more specifically around 3.0 $\mu$m. The tissue to be ablated may be the corneal tissue of the eye.

44 Claims, No Drawings

DUAL BEAM LASER ABLATION

The present invention relates to the laser processing or ablation of tissue, in particular human or animal tissue. This invention is applicable for use in operations on the corneal tissue of the eye for the correction of myopia, myopic astigmatism, hyperopia and other visual problems. These operations are known as photorefractive keratectomy or phototherapeutic keratectomy, and the present invention will therefore be described with reference to its use in such an operation. It is however to be appreciated that other applications are also envisaged.

Currently this operation is performed using excimer lasers operating at wavelengths of 193 nm. The extremely high absorption of excimer laser beams of this wavelength in corneal tissue, and the high photon energy which can directly break molecular bonds therein allows this laser to ablate with very high precision and with virtually no damage to the remaining tissue. However, excimer lasers are bulky and expensive lasers that require significant maintenance and costs to run. These lasers also use a very corrosive gas.

There would therefore be significant benefits in replacing the excimer laser with an alternative laser source. Solid state lasers are available which can produce laser beams at reduced wavelengths of around 200 nm. However, these solid state lasers do not have enough energy to ablate tissue over a large enough area to be useful for this operation. Other lasers are available, such as the Holmium or Erbium laser, which produce a laser beam having very high absorption in corneal tissue and having enough energy to ablate the tissue over a large enough area. However, because the photon energy at the infra-red wavelength of the laser beam produced by these lasers is not high enough to directly break molecular bonds, the tissue adjacent to the ablated zone is damaged to too great an extent to be useful for this operation.

It is therefore an object of the present invention to provide an improved method and apparatus for laser ablation of tissue.

With this in mind, according to one aspect of the present invention, there is provided a method for laser ablation of corneal tissue, including directing at least one first pulsed unfocused laser beam of ultraviolet light and at least one second pulsed unfocused laser beam of infrared light to an area on the tissue to thereby ablate said tissue. The use of pulsed laser beams facilitates the ablation of the tissue while minimising any damage to the surrounding tissue.

The pulses of each said at least one first and second laser beam preferably arrives at the area of the tissue at least substantially simultaneously. This provides for the most efficient ablation of the area of the tissue.

The wavelength of the ultraviolet light may be in the range of between 180 to 225 nm, and the wavelength of the infrared light may be in the range of between 1.4 to 11.0 $\mu$m and most preferably around 3.0 $\mu$m. This is the wavelength closest to the absorption peak of water and hence facilitates the ablation of tissue.

A single first laser beam and/or a single second laser beam may be provided. It is however envisaged that more than one first laser beam and/or second laser beam be provided.

The method may include shifting the frequency of a laser beam of infrared light into the ultraviolet range to thereby provide said first laser beam.

The method may further include producing said first and second laser beams from a first and second laser means respectively, and preferably respectively smoothing, shaping and/or scanning said first and second laser beams.

The first and second laser beams may be mixed or combined to thereby provide a combined laser beam for said ablation. The combined laser beam may also or alternatively be smoothed, shaped and/or scanned.

It is alternatively envisaged that the method may include directing the first and second laser beams from different directions to the ablation area of the tissue.

It is also envisaged that the method may include producing a single laser beam from a laser means and splitting said single laser beam to provide said first and second laser beams. The single laser beam may be smoothed, shaped and/or scanned.

According to another aspect of the present invention, there is provided an apparatus for laser ablation of a corneal tissue, including means for providing at least one first pulsed unfocused laser beam of ultraviolet light, means for providing at least one second pulsed unfocused laser beam of infrared light, and means for directing the first and second laser beams to the area of tissue to be ablated to thereby ablate the tissue. The ultraviolet light and the infrared light may have wavelengths in the range referred to above. Furthermore, a single first laser means and a single second laser means may be provided.

The means for providing the second laser beam may include a second laser means for emitting an infrared laser beam. The second laser means may for example be an Erbium:YAG, $CO_2$ or a Holmium:YAG laser.

In one preferred arrangement according to the present invention, the means for providing the first laser beam may include a first laser means for emitting an ultraviolet laser beam. The first laser means may for example be a mini excimer laser.

In an alternative preferred arrangement according to the present invention, the means for providing the first laser beams may include a first laser means for emitting an infrared laser beam and frequency shifting means for converting the infrared laser beam into the ultraviolet means. The first laser means may for example be a Neodymium:YAG, Titanium:Sapphire, Alexandrite, Erbium:YLF, Erbium:YAG or a Holmium:YAG laser.

In a further preferred arrangement according to the present invention, the apparatus may include a single laser means for emitting an infrared laser beam wherein the means for providing the first and second laser beams includes a first beam splitter for splitting of the infrared laser beam into two laser beam portions, one of the laser beam portions providing the second laser beam, and a frequency shifting means through which the other laser beam portion can pass to thereby provide the first laser beam. The laser means may for example be an Erbium: YAG laser, Titanium:Sapphire, Alexandrite, Neodymium:YAG, Erbium:YLF or a Holmium:YAG laser.

In yet another preferred arrangement according to the present invention, the means for providing the first laser beam may include a first laser means for emitting an infrared laser beam, frequency shifting means for at least substantially converting the infrared laser beam into an ultraviolet laser beam with a portion thereof remaining unshifted, beam splitting means for splitting the unshifted portion of the laser beam from the frequency shifted portion thereof, the shifted portion providing the first laser beam, the unshifted portion thereof pumping a second laser means for providing the second laser beam. The first laser means may for example be a titanium sapphire laser. This laser may be flash lamped pumped. In addition, this laser may optionally be seeded by a short pulse laser. The second laser means may be an Erbium:YAG, $CO_2$ or a Holmium:YAG laser.

The means for directing the first and second laser beams may include beam smoothing means for smoothing the first and second beams respectively, beam shaping means for shaping the first and second laser beams respectively and/or beam scanning means for scanning the first and second laser beams respectively.

The above described apparatus may include means for combining the first and second laser beams into a combined laser beam for directing to said ablation area. The combining means may include a dichroic mirror through which one of said laser beams can pass therethrough and mirror means for reflecting the other of said laser beams to the dichroic mirror, whereby the other said laser beam is reflected at least substantially in the same direction as the said one laser beam to thereby provide said combined laser beams. Smoothing means may be provided for smoothing the combined laser beam. Furthermore, beam shaping means may be provided for shaping the combined laser beam. In addition, beam scanning means may be provided for scanning the combined laser beam.

The corneal tissue may be ablated for the purpose of producing refractive corrections for an eye.

When the ultra-violet and infra-red laser beams are applied to the corneal tissue, the photons of the laser beam of ultra-violet light breaks enough bonds of the corneal tissue to make the ablation process sufficiently efficient to limit damage to the surrounding tissue, whereas the photons of the laser beam of infra-red light provides enough energy to complete the ablation process.

The present invention will be more readily understood from the following description of preferred practical arrangements of the apparatus of the present invention as illustrated in the accompanying drawings:

FIG. 1 is a flow diagram of a first arrangement of an apparatus according to the present invention;

FIG. 2 is a flow diagram of a second arrangement of an apparatus according to a present invention;

FIG. 3 is a flow diagram of a third arrangement of an apparatus according to the present invention; and FIG. 4 is a flow diagram of a fourth arrangement of an apparatus according to the present invention.

Referring initially to FIG. 1, the first arrangement of the apparatus includes an Erbium:YAG laser 1 and a Neodymium:YAG laser 2. The Erbium:YAG laser 1 is a low gain laser providing an infrared (IR) laser beam 11 having a wavelength of 2.94 $\mu$m. This wavelength is closest to the absorption peak of water at 3.0 $\mu$m and therefore able to ablate tissue very well. This IR laser beam 11 initially passes through beam smoothing components 3 of the apparatus before passing through a dichroic mirror 4 which allows transmission of IR light but reflects ultraviolet (UV) light.

The Neodymium:YAG laser 2 also produces an IR laser beam 12. This laser 2 has high power lasing at a wavelength of 1.06 $\mu$m. The fifth harmonic of this laser 2 is 213 nm. It is therefore advantageous and relatively convenient to frequency shift the IR laser beam 12 produced by the Neodymium:YAG laser 2 closer to the desired UV range. This laser beam 12 is therefore initially passed through frequency shifting components 6 which increases the light frequency of the laser beam 12 by a multiple of 5 to thereby bring the laser beam 12 into the UV range. The frequency shifting components 6 may comprise frequency conversion crystals that can frequency double the frequency of the laser beam 12 twice and then mix with the original wavelength to form the fifth harmonic. Other arrangements are also envisaged. The laser beam 12 then passes through beam smoothing components 7 which may for example comprise an arrangement having a spatial filter, optical integrator and/or an image rotator. Such arrangements are used in excimer laser systems and will not be described in detail herein. After passing through the beam smoothing components 7, the laser beam 12 is then reflected off a mirror 8 to a dichroic mirror 4. Because this mirror 4 reflects UV light, this laser beam 12 is reflected in a direction at least substantially parallel to and along the same path as the laser beam 11 from the Erbium:YAG laser 1. This results in at least a degree of mixing of the two laser beams to provide a combined laser beam 13. This combined beam 13 passes through beam shaping components 5 which directs the combined beam 13 the corneal tissue of the eye 10. A computer 9 controls the various components of the apparatus, in particular the two lasers 1, 2 and the beam shaping components 5. These components 5 may comprise a motorised iris diaphragm or masks and other arrangements are also envisaged.

In the arrangement shown in FIG. 2, only one Erbium:YAG laser 20 is required in the apparatus. The IR laser beam 28 from the laser 20 passes through beam smoothing components 21 to a beam splitter 22. This beam splitter 22 splits the IR laser beam 28 into two separate laser beams 30, 29, one light beam 30 passing through frequency shifting components 23 to convert the beam 30 into UV light. This UV laser beam 30 then passes through a dichroic mirror 24 which, unlike the dichroic mirror of the first arrangement, reflects IR light and transmits UV light.

The second IR laser beam 29 is reflected via mirrors 27 to the dichroic mirror 24 which reflects this laser beam 29 in parallel with and along the same path as the UV laser beam 30. As in the first arrangement, the two laser beams are least substantially mixed to provide a combined a laser beam 30a which passes through beam shaping components 25 to the eye 10. A computer 26 controls the operation of the laser 20 and the beam shaping components 25.

In the arrangement shown in FIG. 3, there is provided a mini-excimer laser 32 and a Erbium:YAG laser 31. Mini-excimer lasers use different technology and are less powerful than the excimer lasers normally used. These lasers therefore do not provide enough energy to be used for laser ablation. They are however significantly less expensive and only use small quantities of gas compared with the more powerful excimer lasers. As the gas used is very toxic and corrosive, mini-excimers are therefore safer to use. The mini-excimer laser 32 provides a UV laser beam 36 which passes through beam shaping components 33 directly to the eye 10. The IR laser beam 37 of the Erbium:YAG laser 31 also passes through separate beam shaping components 34 and directly to the eye 10. As the laser beams come from different directions, there is no prior mixing of the laser beams prior to being applied to the eye in this arrangement. Both beam shaping components 34 are controlled by a computer 35.

In the arrangement shown in FIG. 4, there is provided a flash-lamp pumped titanium sapphire laser 40. This laser 40 may optionally also be seeded by a short pulse diode laser (not shown). This provides a shorter pulse width for the emitted laser beam 44 resulting in higher peak powers during the pulse, greater efficiency for the frequency conversion process into UV range and less damage to tissue adjacent to the ablation site.

The laser beam 44 emitted by the titanium sapphire laser is typically within the near IR range typically having a wavelength of between 700 and 800 nm. This laser beam 44 passes through frequency shifting components 41, typically frequency conversion crystals, which twice doubles the frequency of the laser beam 44 such that the laser beam 44a emitted from the frequency shifting components 41 is primarily in the UV range having a wavelength of around 200 nm. A residual portion of the laser beam 44a however remains unshifted in the near IR range.

A beam splitting arrangement 45, typically a dichroic mirror 45, splits the laser beam 44a into a UV laser portion 46 and the frequency unshifted IR portion 47. The latter IR portion 47 pumps an Erbium:YAG laser 42 which, as noted previously, emits a laser beam 50 in the IR range having a wavelength of 2.94 µm.

The UV laser portion 46 is reflected via mirrors 48 to a second dichroic mirror 49. The laser beam 50 from the Erbium:YAG laser 42 is also directed to and passes through the second dichroic mirror 49.

The UV laser portion 46 is reflected by the second dichroic mirror 49 along a path parallel to the Erbium:YAG laser beam 50 to provide a combined laser beam 51. This combined beam 51 passes through a beam smoothing, shaping and scanning arrangement 43 before being directed to the eye 10.

In all of the above arrangements, it is also envisaged that beam scanning means such as a mirror arrangement for scanning the IR and/or UV laser beam or the combined beam also be provided to operate in conjunction with the beam shaping components to scan the beam(s) to the correct position on the eye.

It is to be appreciated that alternative types of lasers are also applicable for use in an apparatus according to the present invention and that the present invention is not restricted to the use of the laser types hereinbefore referred to.

The apparatus of the present invention therefore provides for accurate ablation with tissue damage about the same as a 193 nm excimer laser ablation over a large area of the cornea (more than 1 mm² per pulse) without the need for a normal size excimer laser. This leads to a reduction in overall size of the laser ablation apparatus as well as a significant reduction in the maintenance and running costs for this apparatus without compromising the clinical result.

I claim:

1. A method for laser ablation of corneal tissue comprising directing at least one first pulsed unfocused laser beam of ultraviolet light and at least one second pulsed unfocused laser beam of infrared light to an area on the tissue to thereby ablate said tissue.

2. A method according to claim 1 further comprising timing the pulses of each said at least one first and second laser beams to arrive at the area of the tissue at least substantially simultaneously.

3. A method according to claim 1 wherein the ultraviolet light has a wavelength of between 180 to 225 nm.

4. A method according to claim 1 wherein the infrared light has a wavelength of between 1.4 to 11.0 µm.

5. A method according to claim 4 wherein the wavelength of the infrared light is around 3.0 µm.

6. A method according to claim 1 comprising providing a single said first laser beam or a single said second laser beam.

7. A method according to claim 1 comprising shifting the frequency of a laser beam of infrared light into the ultraviolet range to thereby provide said first laser beam.

8. A method according to claim 1 comprising producing said first and second laser beams from a first and second laser means respectively.

9. A method according to claim 8 further comprising respectively smoothing, shaping and/or scanning said first and second laser beams.

10. A method according to claim 1 comprising combining said first and second laser beams to thereby provide a combined laser beam for said ablation.

11. A method according to claim 10 further comprising smoothing, shaping and/or scanning said combined laser beam.

12. A method according to claim 1 comprising directing the first and second laser beams from different directions to the ablation area of the tissue.

13. A method according to claim 1 further comprising producing a single laser beam from a laser means and splitting said single laser beam to provide said first and second laser beams.

14. A method according to claim 13 comprising smoothing, shaping and/or scanning said single laser beam.

15. A method according to claim 14 comprising a ablating the corneal tissue to thereby produce refractive corrections for an eye.

16. A method according to claim 1 comprising providing a single said first laser beam and a single said second laser beam.

17. An apparatus for laser ablation of a corneal tissue, comprising a means for providing at least one first pulsed unfocused laser beam of ultraviolet light, a means for providing at least one second pulsed unfocused laser beam of infrared light, and a means for directing the first and second pulsed laser beams to the area of tissue to be ablated to thereby ablate said tissue.

18. An apparatus according to claim 17 wherein the pulses of each said at least one first and second laser beams arrives at the area of the tissue at least substantially simultaneously.

19. An apparatus according to claim 17 wherein the ultraviolet light has a wavelength of between 180 to 225 nm.

20. An apparatus according to claim 17 wherein the infrared light has a wavelength of between 1.4 to 11.0 µm.

21. An apparatus according to claim 19 wherein the wavelength of the infrared light is around 3.0 µm.

22. An apparatus according to claim 17 wherein a single said first laser beam and/or a single said second laser beam is provided.

23. An apparatus according to claim 17 wherein said means for providing the second laser beam includes a second laser means for emitting an infrared laser beam.

24. An apparatus according to claim 20 wherein the second laser means is an Erbium: YAG, $CO_2$ or a Holmium:YAG laser.

25. An apparatus according to claim 17 wherein said means for providing the first laser beam includes a first laser means for emitting an ultraviolet laser beam.

26. An apparatus according to claim 23 wherein the first laser means is a mini excimer laser.

27. An apparatus according to claim 17 wherein said means for providing the first laser beam includes a first laser means for emitting an infrared laser beam and frequency shifting means for converting the infrared laser beam into the ultraviolet means.

28. An apparatus according to claim 27, wherein the first laser means is a Neodymium:YAG, Titanium:Sapphire, Alexandrite, Erbium:YLF, Erbium:YAG or a Holmium:YAG laser.

29. An apparatus according to claim 17 further comprising including a single laser means for emitting an infrared laser beam wherein the means for providing the first and second laser beams includes a first beam splitter for splitting of the infrared laser beam into two laser beam portions, one of the laser beam portions providing the second laser beam, and a frequency shifting means through which the other laser beam portion can pass to thereby provide the first laser beam.

30. An apparatus according to claim 28 wherein the laser means is an Erbium:YAG, Titanium:Sapphire, Alexandrite, Neodymium:YAG, Erbium:YLF or a Holmium:YAG laser.

31. An apparatus according to claim 17 wherein the means for providing the first laser beam comprises a first laser means for emitting an infrared laser beam, frequency shifting means for at least substantially converting the infrared laser beam into an ultraviolet laser beam with a portion thereof remaining unshifted, beam splitting means for splitting the unshifted portion of the laser beam from the frequency shifted portion thereof, the shifted portion providing the first laser beam, the unshifted portion thereof pumping a second laser means for providing the second laser beam.

32. An apparatus according to claim 31 wherein the first laser means is a titanium sapphire laser.

33. An apparatus according to claim 32 wherein the titanium sapphire laser is flashed pumped.

34. An apparatus according to claim 32 wherein the titanium sapphire laser is seeded by a short pulse diode laser.

35. An apparatus according to claim 31 wherein the second laser means is an Erbium:YAG, $CO_2$ or a Holmium:YAG laser.

36. An apparatus according to claim 17 wherein the means for directing said first and second laser beams includes beam smoothing means for smoothing the first and second beams respectively.

37. An apparatus according to claim 17 wherein the means for directing said first and second laser beams includes beam shaping means for shaping the first and second laser beams respectively.

38. An apparatus according to claim 17 wherein the means for directing said first and second laser beams includes beam scanning means for scanning the first and second laser means.

39. An apparatus according to claim 17 means for combining the first and second laser beams into a combined laser beam for directing to said ablation area.

40. An apparatus according to claim 39 wherein the combining means comprises a dichroic mirror through which one of said laser beams can pass therethrough and mirror means for reflecting the other of said laser beams to the dichroic mirror, whereby the other said laser beam is reflected at least substantially in the same direction as the said one laser beam to thereby provide said combined laser beams.

41. An apparatus according to claim 39 further comprising a including beam smoothing means for smoothing the combined laser beam.

42. An apparatus according to claim 38 further comprising a beam shaping means for shaping the combined laser beam.

43. An apparatus according to claim 39 further comprising a beam scanning means for scanning the combined laser beam.

44. An apparatus according to claim 17 wherein the apparatus ablates the corneal tissue to thereby produce refractive corrections for an eye.

\* \* \* \* \*

UNITED STATES PATENT AND TRADEMARK OFFICE
CERTIFICATE OF CORRECTION

PATENT NO. : 6,056,741
DATED : May 2, 2000
INVENTOR(S) : Van Saarloos

It is certified that error appears in the above-identified patent and that said Letters Patent is hereby corrected as shown below:

Column 6,
Claim 15, line 15, please delete "comprising a ablating" and insert --comprising ablating-- therefor.
Claim 21, line 34, please delete "claim 19" and insert --claim 20-- therefor.
Claim 24, line 42, please delete "claim 20" and insert --claim 23-- therefor.
Claim 26, line 48, please delete "claim 23" and insert --claim 25-- therefor.
Claim 29, line 60, please delete "including".

Column 7,
Claim 30, line 1, please delete "claim 28" and insert --claim 29-- therefor.

Column 8,
Claim 39, line 5, after "claim 17", please insert --further comprising--.
Claim 41, line 18, please delete "including".
Claim 42, line 20, please delete "claim 38" and insert --claim 39-- therefor.

Signed and Sealed this

Nineteenth Day of June, 2001

*Attest:*

NICHOLAS P. GODICI
*Attesting Officer*    *Acting Director of the United States Patent and Trademark Office*